Figure 1:
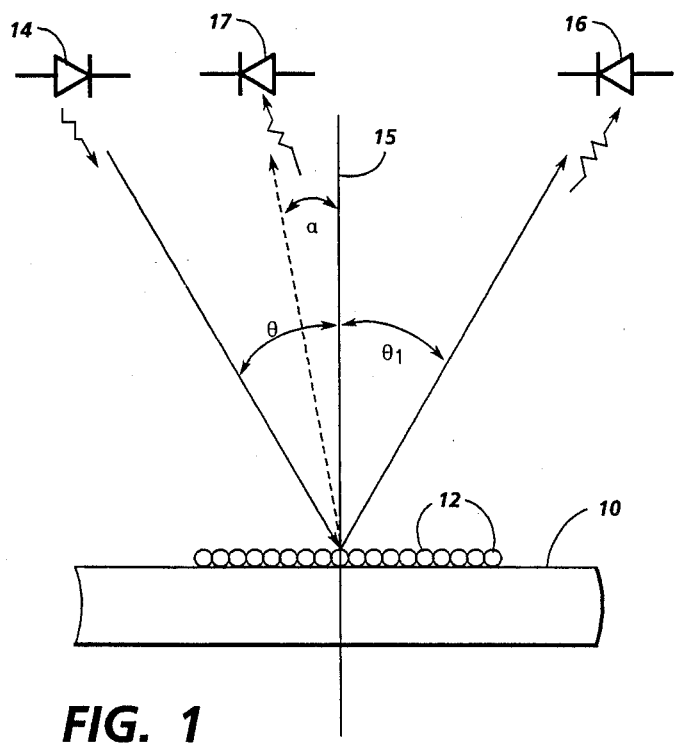

United States Patent [19]
Butler et al.

[11] Patent Number: 4,950,905
[45] Date of Patent: Aug. 21, 1990

[54] COLORED TONER OPTICAL DEVELOPABILITY SENSOR WITH IMPROVED SENSING LATITUDE

[75] Inventors: Michael A. Butler, Rochester; Dusan G. Lysy, Fairport; Paul W. Morehouse, Jr., Webster, all of N.Y.

[73] Assignee: Xerox Corporation, Stamford, Conn.

[21] Appl. No.: 306,112

[22] Filed: Feb. 6, 1989

[51] Int. Cl.$^5$ .............................................. G03G 15/00
[52] U.S. Cl. .................................. 250/358.1; 250/341; 355/246; 356/446
[58] Field of Search .......................... 250/358.1, 341; 356/446, 448; 355/246, 208

[56] References Cited

U.S. PATENT DOCUMENTS

| | | | |
|---|---|---|---|
| 2,956,487 | 10/1960 | Giaimo, Jr. | 95/1.7 |
| 3,094,049 | 6/1963 | Snelling | 95/1.7 |
| 3,734,630 | 5/1973 | McIntosh et al. | 356/448 |
| 3,778,146 | 12/1973 | Knapp | 355/3 |
| 3,801,196 | 4/1974 | Knapp et al. | 355/3 |
| 3,801,349 | 4/1974 | Wilson et al. | 117/31 |
| 4,026,643 | 5/1977 | Bergman | 355/3 DD |
| 4,054,391 | 10/1977 | Witte | 356/209 |
| 4,082,445 | 4/1978 | Steiner | 355/14 |
| 4,178,095 | 12/1979 | Champion et al. | 355/14 R |
| 4,179,213 | 12/1979 | Queener | 355/14 R |
| 4,183,657 | 1/1980 | Ernst et al. | 355/14 R |
| 4,284,356 | 8/1981 | Heilman | 356/429 |
| 4,341,473 | 7/1982 | Mast | 356/446 |
| 4,553,033 | 11/1985 | Hubble, III et al. | 250/353 |
| 4,571,068 | 2/1986 | Tarumi et al. | 355/246 |
| 4,630,918 | 12/1986 | Yui et al. | 355/246 |
| 4,648,702 | 3/1987 | Goto | 355/208 |
| 4,677,298 | 6/1987 | Zelmanovic et al. | 250/358.1 |
| 4,710,627 | 12/1987 | Baltes et al. | 250/341 |
| 4,734,584 | 3/1988 | Rosenthal | 250/358.1 |
| 4,793,710 | 12/1988 | Sapko et al. | 356/446 |
| 4,796,065 | 1/1989 | Kanbayashi | 355/14 E |
| 4,799,082 | 1/1989 | Suzuki | 355/14 R |

Primary Examiner—Constantine Hannaher
Assistant Examiner—Edward J. Glick
Attorney, Agent, or Firm—Mark Costello

[57] ABSTRACT

A non-black colored toner DMA sensor arrangement includes a light emitting device for illuminating a toner/surface substrate with light of a wavelength to which colored toners are non-absorbing, and to which the imaging surface is either partially absorbing or transmissive. Light is reflected from the toner predominantly by either scattering or multiple reflections to produce a significant component of diffusely reflected light. A sensor is arranged for detection of the diffusely reflected light, at an angle that does not detect the specularly reflected component of reflected light. An increasing level of diffusely reflected light indicates an increased density of toner coverage per unit area.

14 Claims, 5 Drawing Sheets

COLORED TONER OPTICAL DEVELOPABILITY SENSOR WITH IMPROVED SENSING LATITUDE

This invention relates generally to reproduction apparatus and more particularly to an arrangement for measuring the amount of unfused colored toner developed onto a substrate.

CROSS REFERENCE

Cross-reference is made to co-pending and earlier filed U.S. patent application Ser. No. 246,242 filed Sept., 19, 1988 and assigned to the same assignee as the present application.

BACKGROUND OF THE INVENTION

In electrophotographic applications such as xerography, a charge retentive surface is electrostatically charged and exposed to a light pattern of an original image to be reproduced to selectively discharge the surface in accordance therewith. The resulting pattern of charged and discharged areas on that surface form an electrostatic charge pattern (an electrostatic latent image) conforming to the original image. The latent image is developed by contacting it with a finely divided electrostatically attractable powder referred to as "toner". Toner is held on the image areas by the electrostatic charge on the surface. Thus, a toner image is produced in conformity with a light image of the original being reproduced. The toner image may then be transferred to a substrate (e.g., paper), and the image affixed thereto to form a permanent record of the image to be reproduced. Subsequent to development, excess toner left on the charge retentive surface is cleaned from the surface. The process is well known and useful for light lens copying from an original and printing applications from electronically generated or stored originals, where a charged surface may be imagewise discharged in a variety of ways. Ion projection devices where a charge is imagewise deposited on a charge retentive substrate operate similarly. While heretofore, toners selected for development have been primarily black, colored toners, for producing full or partial color, highlight color or single non-black color images are becoming an important feature of current copier products.

One important process control in electrophotographic applications is the measurement of the amount of unfused toner that is developed onto the charge retentive surface. In Infrared Reflection Densitometer (IRD) sensors, such as that used for example in the Xerox 1065 copier, heretofore primarily for use with black toners, at a test patch exposed and developed specifically for process control purposes, a light emitting infrared diode illuminates the toner/surface combination, and a photodiode is positioned to collect specularly reflected light. Black toner is light absorbing, so that as more toner is developed onto the surface, the amount of light specularly reflected from the toner/surface combination is attenuated. The process control measurement is the ratio between light reflected from the toner/surface combination and the bare surface. This ratio is referred to as the specular reflection ratio.

It has been found that when specular reflection-based developability sensors are used with colored toners, the specular reflection ratio becomes invariant for DMA (developed toner mass per unit area) values smaller than those associated with optimal control values. For example, it has been noted that when using colored toners with a mean diameter of 9 microns, the specular reflection ratio becomes insensitive to further changes in DMA for DMA values between 0.5 and 0.6 mg/cm$^2$. A desirable DMA sensing range for a colored toner with a mean diameter of 9 microns would extend toward 1.0 mg/cm$^2$. This decrease in sensitivity appears to result from scattering of light by colored toners, since colored toners tend to be poor absorbers of infrared light. It should be also noted that the specular reflection ratio is invariant with a large value compared to zero, as a result of the large angle subtended by the detector, and required to provide latitude in mounting the sensor with respect to the surface. Thus, for colored toners, both specular and diffusely reflected light is detected by the sensor. The diffusely reflected light tends to obscure changes in the specular component, and gives signal saturation at a substantial offset value.

U.S. Pat. No. 4,553,033 to Hubble, III et al. teaches an LCIRD of the type useful for detecting the specular component of reflected light. U.S. Pat. No. 3,801,349 to Wilson et al. teaches a coating density sensor that measures the density of light absorbing powder on a diffusely reflective substrate at a location, preferably at the specularly reflective location. U.S. Pat. No. 2,956,487 to Gaimo, Jr. which, while unclear as to the type of reflected light, appears to be detecting specularly reflected light. U.S. Pat. No. 3,094,049 to Snelling measures toner concentration by measuring transmission of light through toner. U.S. Pat. No. 3,778,146 to Knapp measures toner concentration by measuring transmission of light through toner. U.S. Pat. No. 3,801,196 to Knapp et al. measures toner concentration by measuring light reflected from a reflecting arrangement on a photoconductor, which provides a double pass transmission measurement, at what appears to be a specular reflection angle. U.S. Pat. No. 4,082,445 to Steiner appears to measure reflected light at a test patch for comparison to a clean patch on the photoreceptor. U.S. Pat. No. 4,026,643 to Bergman combines a clean patch/test patch measurement with a measurement of photoreceptor potential with and without charged particle development. U.S. Pat. No. 4,178,095 to Champion et al., U.S. Pat. No. 4,179,213 to Queener, and U.S. Pat. No. 4,183,657 to Ernst et al. all appear to show various aspects of a sensor for the specular component of reflection. U.S. Pat. No. 4,054,391 to Witte discloses a specular reflectance microdensitometer wherein the amount of light specularly reflected by a test surface is correlated to the density of particle coverage on the surface. The reflectance of a clean photoreceptor surface and a toned photoreceptor surface is measured and the ratio determined. U.S. Pat. No. 4,284,356 to Heilman describes light sources and light detectors for illuminating and comparing surface reflectivity.

U.S. patent application Ser. No. 246,242 filed Sept. 19, 1988 and assigned to the same assignee as the present application describes apparatus projecting light rays onto the particles on a surface. Total reflectivity of at least the particles and the diffuse component of the total reflectivity of at least the particles is detected, and a total signal indicative of the total reflectivity of at least the particles and a diffuse signal indicative of the diffuse component of the total reflectivity of at least the particles. The difference between the total signal and the diffuse signal is measured and a signal is generated indicative of the specular component of the total reflectivity of at least the particles.

Certain toners that give the appearance of black toner may be composed of a combination of colored pigments mixed to present a black appearance, rather than carbon black pigments. It is of interest that such toners have retained the light absorbing characteristics of colored toners even though they appear black.

SUMMARY OF THE INVENTION

In accordance with the invention there is provided a method and apparatus for sensing developed mass per unit area (DMA) of toner on an imaging surface, by which toner is illuminated with light of a selected wavelength, and the diffuse component of light reflected from toner/surface combination is sensed as an indication of DMA, where the toner is non-light absorbing for the selected wavelength and the imaging surface is either at least partially absorbing or transmissive.

In accordance with another aspect of the invention, a toner DMA sensor arrangement includes a light emitting device for illuminating a toner/surface substrate with light of a wavelength to which colored toners are non-absorbing, and to which the imaging surface is either partially absorbing or transmissive. Light is reflected from the toner by either scattering or multiple reflections to produce a significant component of diffusely reflected light. A sensor is arranged for detection of the diffusely reflected light, at an angle that should not see the specularly reflected component of reflected light. An increasing level of diffusely reflected light indicates an increased density of toner coverage per unit area.

In accordance with yet another aspect of the invention, a segmented photodiode having center and edge regions separately responsive to the detection of light may be used to detect specularly and diffusely reflected light at the center region and diffusely reflected light at the edge region. It is desirable to measure both components of reflected light since a ratio of specular reflectivity to diffuse reflectivity may be used for calibrating the sensor. Additionally, the device may also serve the dual purpose of sensing light absorbing toner DMA at the center region, when light absorbing toners are in use.

Figure 2:
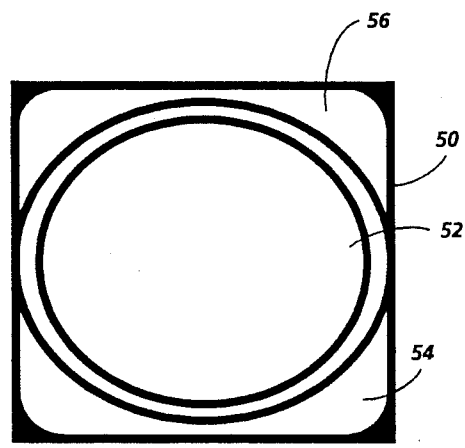
Figure 2A:
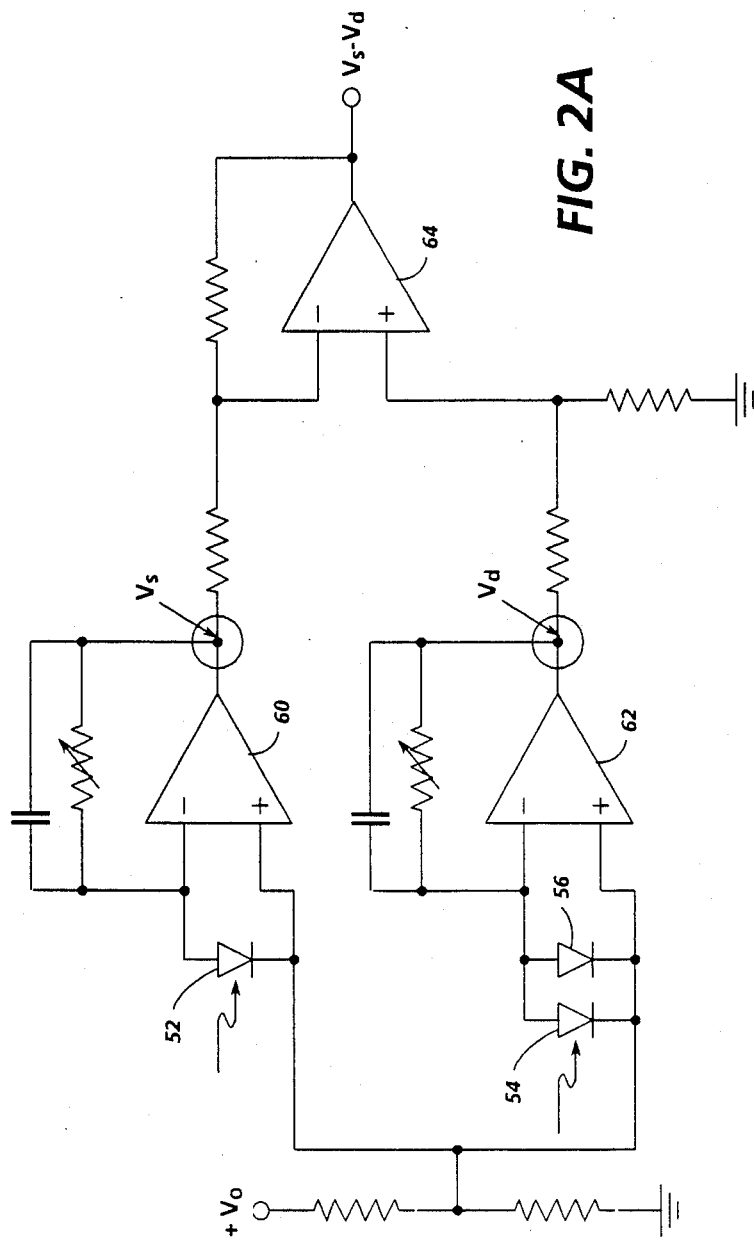
Figure 3:
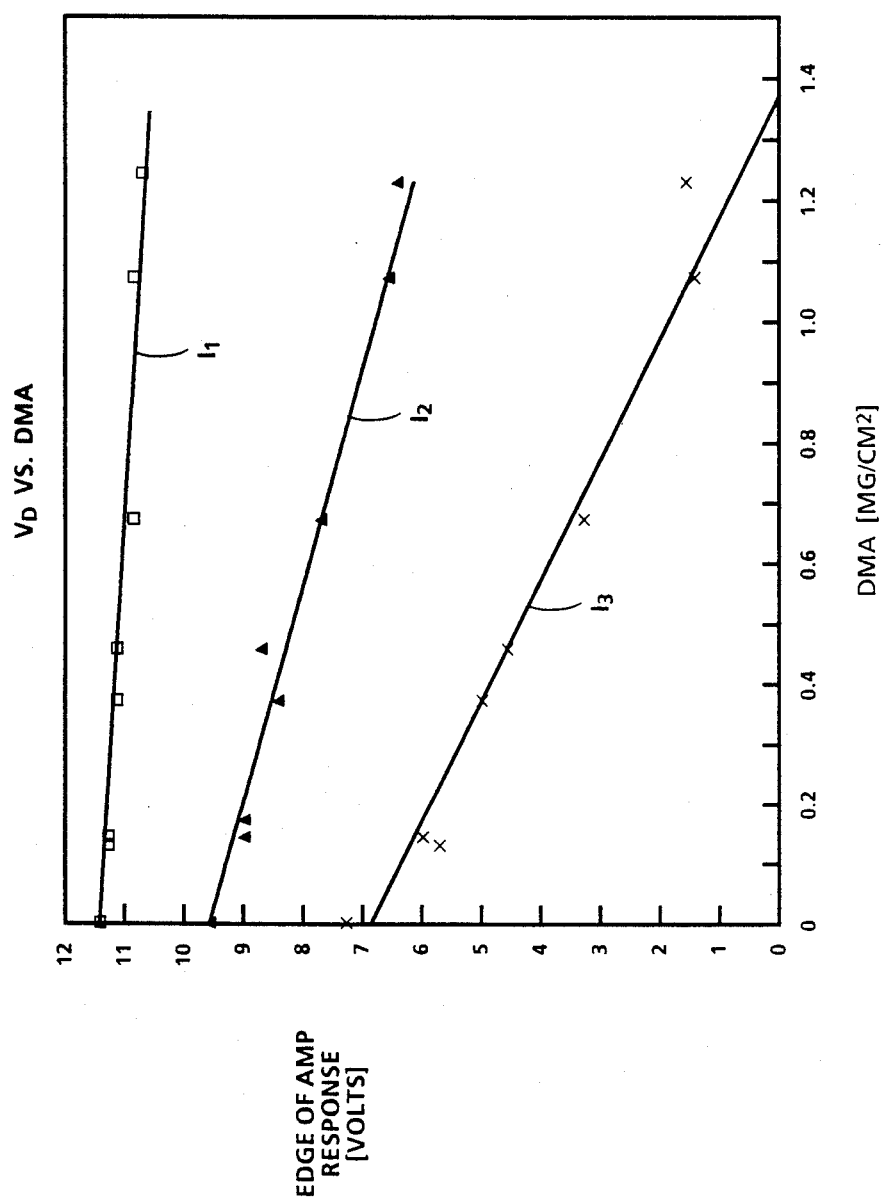
Figure 3A:
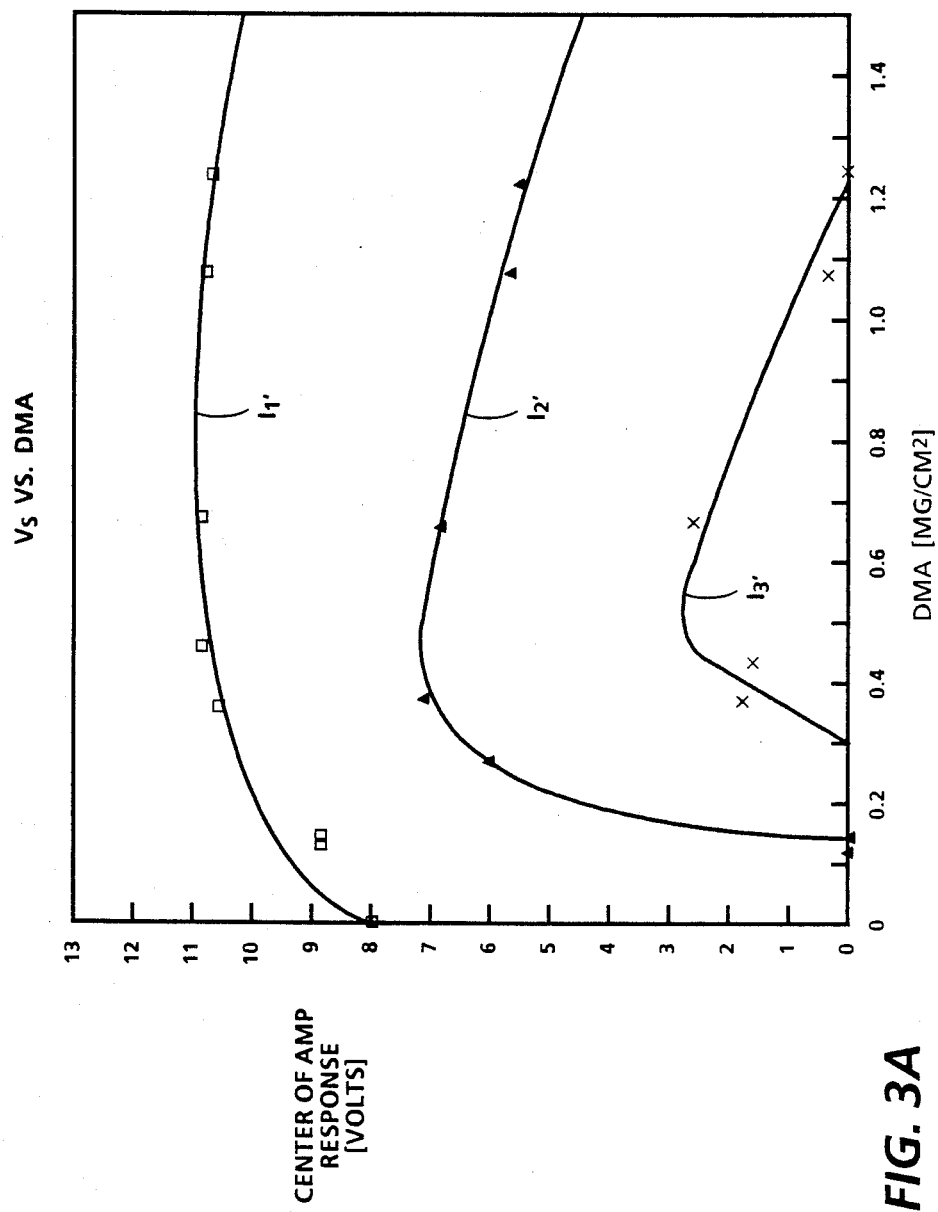
Figure 3B:
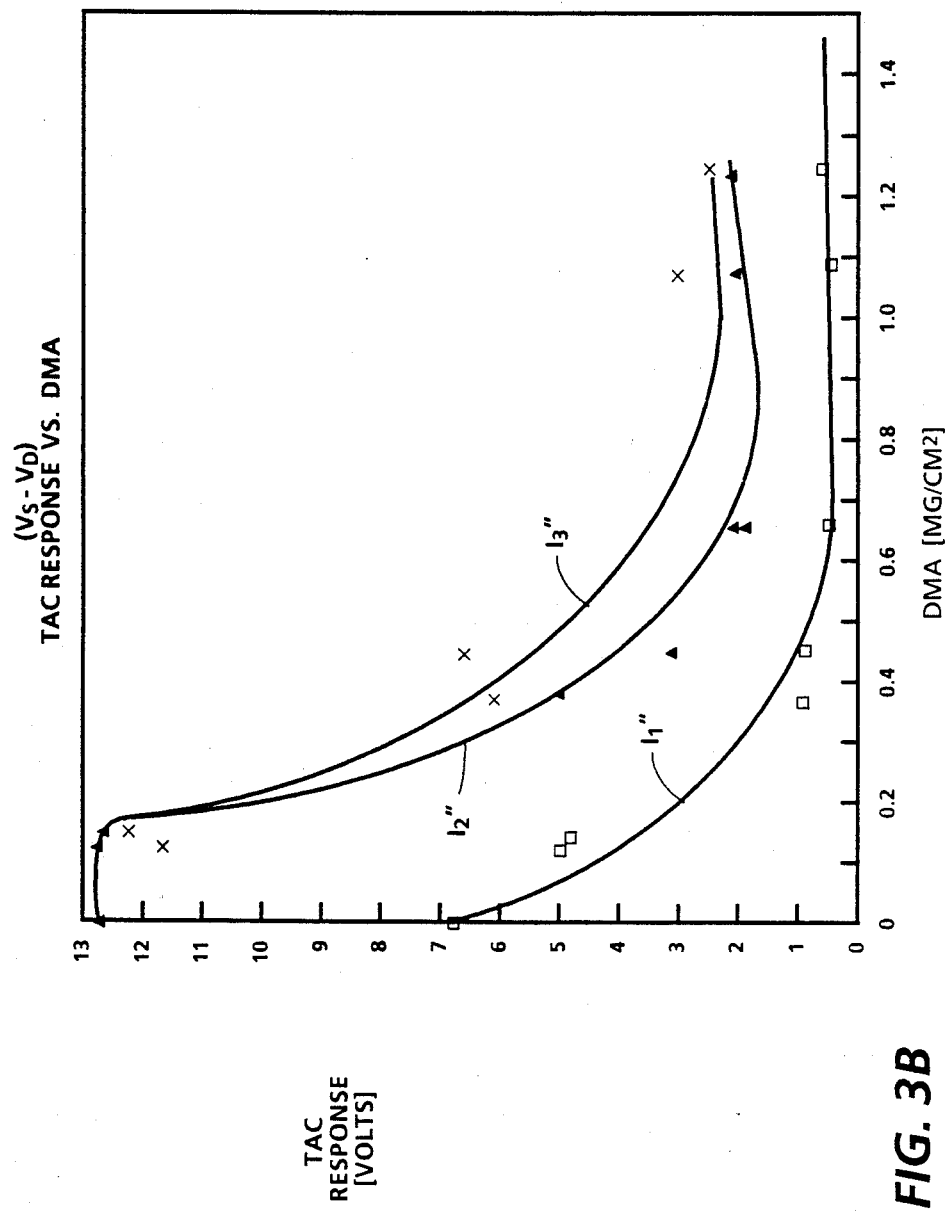

These and other aspects of the invention will become apparent from the following description used to illustrate a preferred embodiment of the invention read in conjunction with the accompanying drawings in which:

FIG. 1 is a somewhat schematic view of a sensor and light source combination for use in detecting the diffuse component of reflection from a toner/imaging surface combination in accordance with the invention;

FIGS. 2 and 2A comprise a toner area coverage sensor for sensing both the specular component of light and the diffuse component of light, and a circuit for producing a signal indicative of sensed DMA; and FIGS. 3, 3A and 3B demonstrate the response characteristics of a DMA sensor that operates to measure the diffuse component of reflected light, the diffuse and specular components of reflected light, and the specular component of reflected light.

Referring now to the drawings, where the showings are for the purpose of describing a preferred embodiment of the invention and not for limiting same, FIG. 1 shows the basic geometric arrangement of a colored toner DMA sensor in accordance with the invention. As used herein, specular reflection refers to that portion of reflected light wherein the angle of reflection is equal to the angle of incidence, and which for an incident beam of collimated light exhibits an angular distribution which is sharply peaked about the specular reflection angle. Diffuse reflection refers to light reflected at angles predominantly other than the specular reflection angle and which for an incident beam of collimated light, exhibits a broad and perhaps isotropic angular distribution. An imaging surface 10 bearing a developed mass of colored toner 12 thereon is illuminated with light source 14 of a selected wavelength. Light source 14 and the wavelength of illumination are selected in conjunction with imaging surface 10 and toner 12 such that the imaging surface is partially absorbing or transmissive, i.e., substantially non-reflective, and the toner is non-light absorbing. For most colored toners and AMAT-type photoreceptors, a light emitting diode produces a satisfactory wavelength of light for this purpose in the near infrared range, and particularly in the range of 800 nm to 1000 nm, although a specific toner may be non-absorbing to other wavelengths of light. Thus, infrared illumination of the toner/imaging surface combination works for most purposes, although where selected colors are used, other illumination wavelengths may be used instead. For discussion purposes, light source 14 is placed at an angle $\theta$ with respect to the normal (indicated by 15) to the imaging surface 10. Accordingly, the specular component of reflected light would be viewed at an angle $\theta_1$, equal in magnitude and opposite in sign to angle $\theta$, and located in the imaginary planes defined by the normal 15 to surface 10, and the position of light source 14. To view the specular component of reflected light, a light detector, such as a photodiode 16, would be located at this angle $\theta_1$ with respect to the angle of incidence. While not necessary to the invention, in practice and for illustration purposes, photodiode 16 may be located along the specular reflection angle for the purpose of sensing light absorbing toner DMA, calibration, or for comparison of clean surfaces response with the colored toner sensor that will be described.

In accordance with the invention, light diffusely reflected from the illuminated toner/imaging surface combination is detected, with a light detector 17. In accordance with the invention, light detector 17 is arranged at an angle $\alpha$, with respect to the normal 15 in such a way that will not provide detection of the specular component of reflection. The light detector, which may be a photodiode or other illumination responsive device, produces an output in response to detected intensity of diffusely reflected light, where increasing density of toner on imaging surface 10 (i.e., increasing DMA) produces increasing intensity of diffusely reflected light.

The angle selected for supporting the diffusely reflected light detector with respect to the light source is based on several factors, including the availability of space, nearness of the light detector to the light source so that sensed light intensity is reasonably measurable, and the desire to provide an optical design that will provide latitude in positioning the sensor relative to the substrate. In comparison to specularly reflected light, the intensity of diffusely reflected light is somewhat less, perhaps suggesting that the output of the light source might be increased, or that careful selection of the position of the light detector is important. Assuming functionality, i.e., that the light detector selected can detect diffuse reflection, there really is no limit to the position of light detector 17 other than the requirement that it not be positioned at the specular reflection angle.

In one possible embodiment, shown in FIGS. 2 and 2A, a photodiode, as described in U.S. patent application Ser. No. 246,242 filed Sept. 19, 1988 and assigned to the same assignee as the present application, and incorporated herein by reference, originally designed for a specularly reflecting light detector for DMA sensing is adapted for sensing diffusely reflected light for colored toner DMA sensing. In its use as a DMA sensor for black toners, the described sensor would normally employ a differential amplifier to separate the diffuse reflection component of the signal acquired at a center photodiode, by subtracting the signal of the edge photodiodes from the signal of the center photodiode. Segmented photodiode 50 is partitioned into a center photodiode 52 and edge photodiodes 54 and 56. Center photodiode 52 detects a combination of specularly reflected and diffusely reflected light. However, the response of edge photodiodes 54 and 56 is separately acquired for the detection of diffusely reflected light. Thus, the photodiode may be centered with the center photodiode 52 at the angle of specular reflection, which places the edge photodiodes 54 and 56 at diffuse reflection angles.

FIG. 2A gives a suggestion for a circuit for driving the photodiodes. Generally, center photodiode 52, and edge photodiodes 54 and 56 provide a signal to operational amplifiers 60 and 62 to produce signals $V_S$ (combined specularly and diffusely reflected light) and $V_D$ (diffusely reflected light), respectively, for the production of an output appropriate for whatever control operations will be accomplished in response to sensor information. If required, described sensor employs a differential amplifier 64 to separate the diffuse reflection component of the signal acquired at a center photodiode 52, by subtracting the signal of the edge photodiodes 54 and 56 from the signal of the center photodiode.

FIGS. 3, 3A and 3B respectively compare detected diffuse reflection, combined specular and diffuse reflection, and isolated specular reflection in comparisons derived from the described sensor. In these tests, samples of 7 micron magenta toner were developed onto an AMAT photoreceptor, and the amplified voltage output from the sensors is compared to measured DMA values. The toner and substrate combination was illuminated with an GaAlAs LED having an output with a peak wavelength near 880 nm. In FIG. 3, a graph of the diffuse reflection response, as measured at edge photodiodes 54 and 56 is shown for increasing light source intensities, derived from the LED by driving it at increasing current values $I_1$, $I_2$, and $I_3$. As previously noted, diffusely reflected light intensities may be expected to be somewhat lower than specularly reflected light intensities, but for all three light intensity values, the response curve varies linearly with DMA. With reference to FIG. 3A, the response curve $I_1'$ from the center photodiode, a combination of the specular and diffuse components of reflection, produced a varying response for DMA from about 0 to 0.7 mg/cm$^2$, and turns over for greater DMA in the range of 0.7 to 1.1 mg/cm$^2$. Curves $I_2'$ and $I_3'$ are believed to represent overdriving operational amps 60, and do not represent desirable curve variations. However, with reference to FIG. 3B, response curve $I_1''$ shows the specular component of reflection, produced by subtracting curve $I_1$ from $I_1'$. Again the specular component demonstrates invariance in the response for DMA over about 0.70 mg/cm$^2$ for $I_1''$.

It will no doubt be appreciated that the output of the described sensor arrangement may be used in a number of ways in machine control or diagnostics.

The invention has been described with reference to a preferred embodiment. Obviously modifications will occur to others upon reading and understanding the specification taken together with the drawings. This embodiment is but one example, and various alternatives modifications, variations or improvements may be made by those skilled in the art from this teaching which are intended to be encompassed by the following claims.

We claim:

1. An electrostatographic imaging device, wherein as part of a dry imaging process, non-light absorbing dry toner is deposited on an imaging surface, and including a toner mass density measuring arrangement comprising:
   a light source, arranged to illuminate the toner deposited on the imaging surface, and having an output wavelength selected so that the light is substantially not absorbed by the toner, and is substantially not reflected by the surface; and
   a light detector for detecting the intensity of light of the selected wavelength reflected from the toner and imaging surface combination, and positioned with respect to the surface and light source to detect the diffuse component of reflected light, while excluding from detection any specular component of reflected light, with an increased intensity of diffusely reflected light indicating increased toner mass density.

2. An imaging device as defined in claim 1 wherein said selected output wavelength is in the near infrared range.

3. An imaging device as defined in claims 2 wherein said selected output wavelength is in the range of 800 to 1000 nanometers.

4. An imaging device as defined in claim 1 and including a second sensor positioned with respect to the surface and light source to detect the specular component of the reflected light.

5. A dry toner mass density measuring arrangement, for measuring non-light absorbing toner density on a surface comprising:
   a light source, having an output wavelength selected so that the light is substantially not absorbed by the toner, and is substantially not reflected by the surface; and
   a light detector for detecting the intensity of light of the selected output wavelength, reflected from the toner and surface combination, and positioned with respect to the surface and light source to detect the diffuse component of the reflected light while excluding from detection any specular component of reflected light, with an increased intensity of diffusely reflected light indicating increased toner mass density.

6. A dry toner mass density measuring arrangement as defined in claim 5 wherein said selected output wavelength is in the near infrared range.

7. A dry toner mass density measuring arrangement as defined in claim 6 wherein said selected output wavelength is in the range of 800 to 1000 nanometers.

8. A dry toner mass density measuring arrangement as defined in claim 5 wherein the light source is a light emitting diode having an output wavelength in the near infrared range.

9. A dry toner mass density measuring arrangement as defined in claim 8 wherein said selected output wavelength is in the range of 800 to 1000 nanometers.

10. A dry toner mass density measuring arrangement as defined in claim 5 and including a second light detector for detecting the intensity of light of the selected output wavelength positioned with respect to the surface and light source to detect the specular component of the reflected light.

11. A toner mass density measuring arrangement, for measuring non-light absorbing toner density on a imaging surface comprising:
   a light emitting diode, having an output wavelength selected so that the light is substantially not absorbed by the non-light absorbing toner, and is substantially not reflected by the imaging surface;
   a segmented photodiode having at least two portions, each independently producing a response to detected light intensity, including a center portion and an edge portion;
   said diode positioned with respect to the surface and light source to detect a combination of specularly and diffusely reflected light at the center portion and only diffusely reflected light at the edge.

12. A toner mass density measuring arrangement as defined in claim 11 wherein the light source is a light emitting diode having an output wavelength in the near infrared range.

13. A toner mass density measuring arrangement as defined in claim 12 wherein said selected output wavelength is in the range of 800 to 1000 nanometers.

14. A toner mass density measuring arrangement as defined in claim 11 and including means for subtracting the diffuse component of reflection from the combination of specularly reflected and diffusely light to isolate the specular component of reflection.

* * * * *